United States Patent

Kato et al.

[11] Patent Number: 5,256,769
[45] Date of Patent: Oct. 26, 1993

[54] MUTUAL SEPARATION OF PROTEINS

[75] Inventors: Koichi Kato, Kawabe; Takao Yamada, Matsubara; Kenji Kawahara, Izumi, all of Japan

[73] Assignee: Takeda Chemical Industries, Ltd., Osaka, Japan

[21] Appl. No.: 774,811

[22] Filed: Sep. 11, 1985

[30] Foreign Application Priority Data

Sep. 26, 1984 [JP] Japan .................. 59-00460
May 21, 1985 [JP] Japan .................. 60-00274

[51] Int. Cl.$^5$ .......................... C07K 13/00; C07K 3/28
[52] U.S. Cl. ................................ 530/351; 530/300; 530/364; 530/399; 530/350; 530/380; 530/412; 530/416; 530/417; 530/806; 530/808; 530/820; 530/827; 435/69.1; 435/69.3; 435/69.4; 435/69.5; 435/69.6; 435/183
[58] Field of Search ............... 530/412, 416, 417, 350, 530/300, 351, 138, 364, 399, 806, 808, 820, 827, 68, 70, 183; 435/69.1, 69.3, 69.4, 69.5, 69.6

[56] References Cited

U.S. PATENT DOCUMENTS

| | | | |
|---|---|---|---|
| 4,503,035 | 3/1985 | Pestka et al. | 530/351 |
| 4,658,021 | 4/1987 | Goeddel et al. | 530/399 |
| 4,736,020 | 4/1988 | Hillen et al. | 530/351 |
| 4,746,647 | 5/1988 | Swenson et al. | 424/92 |
| 4,798,886 | 1/1989 | Kato et al. | 530/417 |

FOREIGN PATENT DOCUMENTS

| | | |
|---|---|---|
| 0043980 | 1/1982 | European Pat. Off. |
| 0088195 | 12/1982 | European Pat. Off. |
| 0089692 | 3/1983 | European Pat. Off. |
| 0091539 | 3/1983 | European Pat. Off. |
| 0094317 | 5/1983 | European Pat. Off. |
| 092163 | 10/1983 | European Pat. Off. |
| 0109748 | 10/1983 | European Pat. Off. |
| 0111344 | 12/1983 | European Pat. Off. |
| 0132359 | 7/1984 | European Pat. Off. |
| 0117470 | 9/1984 | European Pat. Off. |
| 0118617 | 9/1984 | European Pat. Off. |
| 0145390 | 11/1984 | European Pat. Off. |
| 0147819 | 12/1984 | European Pat. Off. |
| 8505631 | 12/1985 | PCT Int'l Appl. |
| 8601229 | 2/1986 | PCT Int'l Appl. |

OTHER PUBLICATIONS

Kato, K. et al, Biochem. & Biophys. Comm. 130:2 (Jul. 31, 1985) 692–699.
Urushizaki, I., et al, Biochimica et Biophysica Acta, 243 (1971) 187–193.
Pharmacia, FPLC Ion Exchange & Chromatofocusing, 28–37, (1985).
Tsugawa, R., BioFair Tokyo '86, (Oct. 1986) 18, 113–118.
Tsuji, T., et al., Biochem. 26, 3129–3134 (1987).
Staehelin, T., et al, Journal of Biol. Chem. 256: 18, 9750–9754, (1981).
Moriya et al CA vol. 105, 1986, #207347a.
Yamada et al, CA vol. 104, 1986, #205032z.
J. Interferon Res. 1, 381–390 (1981).
The Peptides, ed Grass et al, 1983 (vol. 5) 39–40.
Richey, *Am. Lab.* 1982.
Fagerstam et al, *J. Chrom.* 266, 1983 pp. 523–532.
Journal of Chromatography, 266 (1983) 523–532.

*Primary Examiner*—Garnette D. Draper
*Attorney, Agent, or Firm*—David G. Conlin; Ronald I. Eisenstein

[57] ABSTRACT

A protein of interest or a Met-protein, e.g. the N-Met analog of the protein of the interest can be efficiently separated from a mixture thereof by subjecting the mixture to a separation procedure utilizing the difference in the isoelectric points between the protein and the Met-protein.

32 Claims, 7 Drawing Sheets

```
          1
X-Ala Pro Thr Ser Ser Ser Thr Lys Lys Thr Gln Leu Gln

20
Leu Glu His Leu Leu Leu Asp Leu Gln Met Ile Leu Asn

Gly Ile Asn Asn Tyr Lys Asn Pro Lys Leu Thr Arg Met

40
Leu Thr Phe Lys Phe Tyr Met Pro Lys Lys Ala Thr Glu

60
Leu Lys His Leu Gln Cys Leu Glu Glu Glu Leu Lys Pro

Leu Glu Glu Val Leu Asn Leu Ala Gln Ser Lys Asn Phe

80
His Leu Arg Pro Arg Asp Leu Ile Ser Asn Ile Asn Val

100
Ile Val Leu Glu Leu Lys Gly Ser Glu Thr Thr Phe Met

Cys Glu Tyr Ala Asp Glu Thr Ala Thr Ile Val Glu Phe

120
Leu Asn Arg Trp Ile Thr Phe Cys Gln Ser Ile Ile Ser

133
Thr Leu Thr
```

FIG. I

```
                1
X-Cys Asp Leu Pro Gln Thr His Ser Leu Gly Ser Arg Arg
                              20
Thr Leu Met Leu Leu Ala Gln Met Arg Lys Ile Ser Leu

Phe Ser Cys Leu Lys Asp Arg His Asp Phe Gly Phe Pro
 40
Gln Glu Glu Phe Gly Asn Gln Phe Gln Lys Ala Glu Thr
                                    60
Ile Pro Val Leu His Glu Met Ile Gln Gln Ile Phe Asn

Leu Phe Ser Thr Lys Asp Ser Ser Ala Ala Trp Asp Glu
     80
Thr Leu Leu Asp Lys Phe Tyr Thr Glu Leu Tyr Gln Gln
                                100
Leu Asn Asp Leu Glu Ala Cys Val Ile Gln Gly Val Gly

Val Thr Glu Thr Pro Leu Met Lys Glu Asp Ser Ile Leu
         120
Ala Val Arg Lys Tyr Phe Gln Arg Ile Thr Leu Tyr Leu
                                          140
Lys Glu Lys Lys Tyr Ser Pro Cys Ala Trp Glu Val Val

Arg Ala Glu Ile Met Arg Ser Phe Ser Leu Ser Thr Asn
             160               165
Leu Gln Glu Ser Leu Arg Ser Lys Glu
```

1 P2
2 P1
3 NON-GLYCOSYLATED HUMAN IL-2

MUTUAL SEPARATION OF PROTEINS

BACKGROUND

The present invention relates to a method for the mutual separation of proteins, i.e. the separation of proteins from each other.

It is well known that various physioactive proteins, such as cytokines and peptide hormones, exist. The current progress of gene engineering techniques is making way for the mass production and clinical application of these physioactive proteins.

Such techniques have already been applied to provide production of a wide variety of physiologically active proteins, including cytokines, such as interferons, interleukins, B cell growth factor, B cell differentiation factor, macrophage activating factor, lymphotoxin, tumor necrosis factor, etc., peptide hormones, such as erythropoietines, epithelial cell growth factor, insulin, human growth hormone, transforming growth factor, etc., antigenic proteinaceous materials useful in developing vaccines against pathogenic microorganisms, such as hepatitus B virus antigen, influenza antigen, foot-and-mouth disease virus antigen, malarial parasite antigen, etc., enzymes such as peptidases (e.g., tissue plasminogen activator, urokinase, serratiopeptidase, etc.), lysozyme, etc., hemoproteins, such as human serum albumin, etc., and other proteins having useful physiological properties.

However, where such proteins have been produced by recombinant methods, there have been problems experienced in separating the ultimate desired product from other materials with which it is often mixed. A particularly vexing problem has been caused by the fact that the expression product obtained by expression of the gene coding for the protein of interest often contains a mixture of the protein of interest and a second protein, the second protein comprising the protein of interest bound to an extraneous methionine group at its amino terminus The extraneous methionine (Met) group comes from the expression of the ATG start codon which signals the start of expression of the desired gene, and the failure of the expression system of the host cell to excise the extraneous Met group from the expression product. This problem can occur in both prokaryotic hosts and eukaryotic hosts, but most often occurs in expression of genes in prokaryotic hosts. It is a particular problem in expression systems utilizing *Eschericia coli* as expression host.

Because protein synthesis in both eukaryotes and prokaryotes starts at the mRNA codon AUG, which codes for the amino acid methionine, it is not unexpected that the protein expression produces a mixture of molecular species, namely the protein of interest and its analogs with an extraneous Met at the N-terminus (N-Met analog), particularly when the expression host is *Escherichia coli*.

In fact, it is known that IF-3, an *Escherichia coli* initiation factor, includes two molecular species, i.e. the one species possessing a methionine residue at the amino terminus and the other without a mechionine as the terminal residue [Hoppe Seyler's Z. Physiol. Chem., 354, 1415 (1973)], and that the amino terminus of *Escherichia coli* proteins is commonly methionine [Conn & Stumpf (1976), Outlines of Biochemistry, 4th edition, John Wiley & Sons]. The problem of production of high ratios of the Met analog to the desired protein produced by recombinant DNA technology has also been widely experienced. See, e.g., Nature, 293, 408 (1981), wherein the production of human growth hormone resulted in a large ratio of the Met analog to the actual desired protein.

Where a mixture of the desired protein and its N-Met analog are produced, it is extremely difficult to separate one from the other, because the two molecular species differ little, if at all, in their physicochemical properties.

The methionine residue is an amino acid residue with a molecular weight of approximately 131 and with a medium hydrophobicity and it is electrically neutral because of the lack of dissociative groups. In addition, protein is a macromolecule possessing many dissociative groups, hydrophobic groups, and hydrophilic groups. For example, the molecular weight of the interleukin-2 polypeptide (I) shown in FIG. 1, which is composed of 133 amino acid residues (where X means a hydrogen atom), is approximately 15,420. Therefore, it is expected that the addition of one methionine residue to the amino terminus of protein normally does not greatly affect the physicochemical properties of the protein itself. Thus it can be extremely difficult to separate the molecular species to which a methionine residue has been added at the amino terminus and that without the terminal methionine residue from each other.

While this difficulty is common to many proteins, the difficulties have been particularly acute in attempts at separating recombinant interleukin-2 and recombinant interferon from their N-Met analogs, especially when the recombinant proteins have been expressed using *Escherichia coli* as the host for the expression.

Interleukin-2, one of the lymphokines which are produced by the T cells activated by mitogens or antigens, is a factor essential to the growth and differentiation of cytotoxic T cells and natural killer cells and it exerts an important action in the immunoreaction system mediated by these cells.

Interferon-α, a kind of the lymphokines which are produced by the leukocytes activated by viruses or nucleic acids, has a bioactivity of acting on cells to put them into the antivirus state and it exerts an important action in the antiinfection system and oncoimmunity system.

It is expected that interleukin-2 and interferon-α can be effectively used as therapeutics for immune deficiency diseases, infectious diseases, malignant tumors etc. because of their bioactivities. The natural interleukin-2 which has been isolated from the supernatant of the culture of human peripheral blood lymphocytes or human T cell leukemia cells (Jurkat line), includes a few molecular species with different molecular weights; however, it is known that all of them resemble each other very much with regard to the polypeptide chain composition, e.g., their amino terminus is an alanine residue without exception [Japanese Patent Application No. 149248/1984 (Filing Date: Jul. 19, 1984) which corresponds to EP Publication (laid open) No. 032359; Pro. Natl. Acad. Sci. USA, 81, 2543 (1984)].

The natural interferon-α which has been isolated from the supernatant of the culture of human leukocytes, includes ten or more subtypes; however, all of them resemble to each other very much with regard to the polypeptide chain composition, e.g., their amino terminus is a cysteine residue without exception [Arch. Biochem. Biophys., 221, 1, (1983)].

The present inventors have succeeded in producing non-glycosylated human interleukin-2 by expressing the human lymphocyte interleukin-2 gene in *Escherichia coli* cells by means of recombinant DNA technology [Japanese Patent Application No. 225079/1983 (Filing Date: Nov. 28, 1983) which corresponds to EP Publication (laid open) No. 0145390]. The said interleukin-2 contains polypeptide (I), which possesses the amino acid sequence shown in FIG. 1 (in the figure, X means a hydrogen atom or a methionine residue), and it includes two molecular species, i.e., the one species whose amino terminus is an alanine residue as in natural human interleukin-2 (i.e. X is a hydrogen atom) and the other whose amino terminus is a methionylalanine residue to which a methionine residue has been added at the amino terminus (i.e. X is a methionine residue).

As previously reported [J. Interferon Res., 1, 381 (1981); J. Biol. Chem., 256, 9750 (1981)], interferon-$\alpha$A which has been expressed in *Escherichia coli* cells by means of recombinant DNA technology, for example, contains the polypeptide possessing the amino acid sequence shown in FIG. 2, and it includes two molecular species, i.e. the one species whose amino terminal amino acid is a cysteine residue as in natural human interferon-$\alpha$ (i.e. X is a hydrogen atom) and the other whose amino terminal amino acid is a methionyl-cysteine residue to which a methionine residue has been added at the amino terminus (i.e. X is a methionine residue).

It is possible that the highly ordered conformation of protein differs between the molecular species to which a methionine residue has been added at the amino terminus and that without a methionine as the terminal residue; therefore, it is also possible that the bioactivities or biological stability in vivo and in vitro are different between the two. In addition, the addition of a methionine residue to the amino terminus may cause the increase or decrease in antigenicity. Consequently, from the point of view of physiological and industrial application, it is highly desirable to obtain practically pure molecular species by separating the molecular species to which a methionine residue has been added at the amino terminus and that without a methionine as the terminal residue from each other.

The ratio of the addition of a methionine residue to the amino termini may be affected by culture conditions or protein expression levels [J. Interferon Res., 1, 381 (1981)]; however, no example has been reported yet where the ratio of the addition of a methionine residue was successfully controlled. Likewise, no example has been reported yet where the molecular species to which a methionine residue had been added at the amino terminus and that without the terminal methionine residue were separated from each other in the protein purification process.

The present inventors could not separate either (a) an interleukin-2 possessing a methionine residue at the amino terminus and the protein without the terminal methionine residue, or (b) the interferon-$\alpha$A possessing a methionine residue at the amino terminus and that without the methionine terminal residue, from each other, respectively, although many methods were tried as a method for the mutual separation, e.g. salting-out and solvent precipitation, where the difference of solubility is utilized, dialysis, ultrafiltration, gel filtration, and SDS-polyacrylamide gel electrophoresis, where the difference of molecular weight is mainly utilized, affinity chromatography which utilizes the specific affinity of antibody for the proteins, and reversed-phase high performance liquid chromatography, where the difference of hydrophobicity is utilized.

SUMMARY OF THE INVENTION

The present inventors have found that proteins and their N-Met analogs unexpectedly have different isoelectric points and can be separated from each other on that basis. One skilled in the art would have thought, if methionine is added to the amino terminus of protein, the electric charge of the entire protein would not be affected, because methionine is an electrically neutral amino acid. Therefore, it was an unexpected discovery that proteins such as interleukin-2 and the interleukin-2 possessing a metionine residue added to the amino terminus have different isoelectric points.

DETAILED DESCRIPTION OF THE INVENTION

The object of this invention is to provide a method of separating either a protein of interest or its N-Met analog from a mixture comprising the protein and its N-Met analog, the N-Met analog comprising an amino acid sequence which is sufficiently similar to the amino acid sequence of the protein of interest to provide a physiological activity provided by the protein and the N-Met analog bearing an additional methionine residue at its amino terminus as compared to the protein, which comprises subjecting the mixture to a separation procedure utilizing the difference in the isoelectric points between the protein and its N-Met analog.

As used in the present specification, the term "protein" means polymeric materials composed primarily of amino acids, and includes polypeptides, whether or not glycosylated or otherwise chemically or structurally modified, e.g. by chemical or enzymatic reactions, many of which are known per se in the art.

As used in the present specification, the term "Met-protein" means a protein having a methionine group attached at its amino terminus. The invention is especially directed to Met-proteins which have physiological activity which is the same as or similar to the physiological activity of the protein of interest. Thus preferred Met-proteins dealt with in accordance with the present invention are those which comprise an amino acid sequence which is sufficiently similar to the amino acid sequence of the protein of interest to provide a physiological activity provided by the protein of interest. The invention is particularly directed to methods and products relating to the separation of proteins from Met-proteins which are the N-Met analogs of the proteins of interest. In particularly preferred embodiment the invention is directed to separation of interleukin-2 protein from their N-Met analogs and to separation of interferon-$\alpha$ protein from their N-Met analogs.

As used in the present application, the term "physiological activity" means evidencing an activity or effect on organisms and/or biological materials, including cells, parts of cells, products of cellular or other biological activity, and other biological materials whether or not such materials are living, in vivo or in vitro, including both biological and immunological activities and effects.

As the above-mentioned mixture comprising "protein" and "Met-protein" can be usually produced by means of gene recombination technology, that is, by putting *Escherichia coli*, *Bacillus subtilis*, yeast, or animal cells, into protein expression.

As the said "protein", various physioactive proteins are mentioned as follows: cytokines such as interferons (IFNs; IFN-α, IFN-β, IFN-γ etc.), interleukins (interleukin-1, interleukin-2 etc.), B cell growth factor (BGF), B cell differentiation factor (BDF), macrophage activating factor (MAF), lymphotoxin (LT), and tumor necrosis factor (TNF); transforming growth factor (TGF-α); peptide hormones such as erythropoietines, epithelial cell growth factor, insulin, and human growth hormone; antigenious proteins of pathogenic microorganism such as hepatitis B virus antigen, influenza antigen, foot-and-mouth disease virus antigen, and malarial parasite antigen; enzymes such as peptidases (e.g. tissue plasminogen activator, urokinase, and serratiopeptidase) and lysozyme; and hemoproteins such as human serum albumin (HSA).

Among these proteins, to those with a molecular weight of about 3,000–50,000, especially of about 5,000–30,000 or with about 30–500 amino acids, especially with about 50–300 amino acids, the mutual protein separation method of the present invention can be advantageously applied.

The present mutual separation method can be effectively applied to the proteins with an isoelectric point of about 4–11, especially of about 5–8, and it is preferable that the difference of isoelectric point is at least about 0.01, preferably at least 0.1, most preferably 0.01–0.2 between a protein and the protein possessing a methionine residue at the amino terminus.

The separation method of the present invention can be applied especially to interleukin-2 and interferon-α produced by means of gene recombination technology.

In this case, any interleukin-2 species possessing the biological or immunological activity similar to that of natural human interleukin-2 or its derivatives or modifications, such as binding activity with interleukin-2 receptor and antiinterleukin-2 antibody, can be used as the interleukin-2. To describe concretely, the polypeptide possessing the amino acid sequence shown in FIG. 1 (Polypeptide I; where, X means a hydrogen atom) and the fragments with a partial amino acid sequence essential to the biolgcical or immunological activity of the polypeptide, can be employed. For example, the fragment where one amino acid has been lost (EP Publication (laid open) No. 91539) and the fragment where four amino acids have been lost at the amino terminus of Polypeptide (I) [Japanese Patent Application No. 235638/1983, (Filing Date: Dec. 13, 1983)] which is published as Japanese Patent Publication (laid open) 126088/1985, and the fragment lacking several amino acids at the carboxyl terminus, can be accepted. The fragments where one or more amino acids composing the said polypeptide (I) have been lost or replaced by another (other) amino acid(s), such as the fragment where the 125th cysteine residue has been replaced by a serine residue (Japanese Patent Publication (laid open) No. 93093/1984) which corresponds to EP Publication (laid open) No. 109748, are also acceptable. It is preferable that these polypeptides are non-glycosylated polypeptides, especially IL-2 possessing the amino acid sequence shown in FIG. 1.

Hereinafter in some cases, these interleukin-2s are abbreviated to IL-2 and the interleukin-2 possessing one methionine residue added to the amino terminus to Met-IL-2.

In the present invention, any interferon-α species possessing the biological or immunological activity similar to that of natural human interferon-α such as the binding activity with interferon-α receptor or anti-interferon-α antibody, can be employed as the interferon-α. For example, the polypeptide with the amino acid sequence shown in FIG. 2 (polypeptide-II: where, X means a hydrogen atom) is used. Moreover, the fragments consisting of a partial amino acid sequence essential to the biological or immunological activity of interferon-α can be accepted; for example, the fragments lacking several amino acids at the amino terminus of the interferon-α A polypeptide (II) and those lacking several amino acids at the carboxyl terminus can be employed. The fragments where one or more amino acids composing the said polypeptide (II) have been lost or replaced by another(other) amino acid(s) are also acceptable. Interferon-αA is most preferable. It is favorable that these polypeptides are unglycosylated polypeptides.

Hereinafter in some cases, these interferon-αAs are abbreviated to IFN-αA and the interferon-α A possessing a methionine residue at the amino terminus to Met-IFN-αA.

As the said mixtures comprising proteins and Met-proteins, mixed proteins having a purity of at least about 50%, preferably of more than about 80%, most preferably of about 99%, can be employed.

The present invention makes it possible to isolate these proteins by subjecting the said mixture to the separation procedure based on the difference of their isoelectric points.

In accordance with the method described in Example 1, the isoelectric point has been determined as 7.7 and 7.5 for IL-2 and Met-IL-2, respectively.

In accordance with the method described in Example 6, the isoelectric point has been determined as 6.2 and 6.3 for IFN-αA and Met-IFN-αA, respectively.

In the present invention, any technique where the proteins whose isoelectric point is different from each other by 0.01 to 0.2 or so, are isolated from each other, is applicable as the separation procedure based on the difference of isoelectric point. For example, techniques known per se and the combinations of them can be applied, such as the techniques where proteins are subjected to migration in an electric field, which include density gradient isoelectric electrophoresis using Ampholines, gel isoelectric electrophoresis, isotachophoresis etc.; and those techniques where proteins are attached to a charged carrier, e.g. in an elution column, and eluted separatedly in accordance with the charge difference which is brought about by the difference of their isoelectric points, by producing a pH gradient or a salt concentration gradient in the carrier. Such methods include chromato focusing, FPLC (Fast Protein Liquid Chromatography), DEAE (diethylaminoethyl)-CM (carboxymethyl) or SP (sulphopropyl)-ion exchange chromatography, can be employed. All of the reagents and instruments used in these separation procedures are commercially available. For example, Ampholine is available from LKB (Sweden), the gels used in gel isoelectric fractionation from Pharmacia (Sweden) as Sephadex LEF and from LKB (Sweden) as PAG (polyacrylamide gel) plates, carriers and elution buffers for chromato focusing from Pharmacia (Sweden) as polybuffer exchangers PBE94/PBE118, Polybuffer 74, and Polybuffer 96, Mono-P columns, Mono-Q columns, and elution buffers used in FPLC from Pharmacia (Sweden), DEAE ion exchangers from Toyo Soda Manufacturing (Japan) as DEAE-Toyopearl, QAE ion exchangers from Toyo Soda Manufacturing (Japan) as CM- Toyopearl, and SP ion exchangers from Toyo Soda Manufacturing (Japan) as SP-5PW and from Pharmacia (Sweden) as SP-Sephadex [see Methods in Enzymology 5, 3-27(1962), the disclosure of which is incorporated herein by reference].

In the gel isoelectric electrophoretic isolation techniques, commercially available materials such as PAG plates (245×110×1 mm, LKB) e.g. plates for pH 3.5-9.5, plates for pH 5.5-8.5 etc. may be used as plates, and known materials such as 1M phosphoric acid, or 0.4M HEPES buffers etc. may be as the anode liquid, and known materials such as 1M sodium hydroxide, or 0.1M aqueous solution of sodium hydroxide etc. may be as the cathode liquid. The usual conditions suitable for the operation are:

Protein amount: 10–1,000 μg per plate
Electric power: 1–200 W, preferably 10–50 W
Temperature: 0°–20° C., preferably 2–5° C.
Migration time: 0.5–50 hrs, usually 1.5–5 hrs.

In the FPLC techniques, known materials such as a Mono-P column (0.5×20 cm, Pharmacia) may be used, known buffers such as 0.025M diethanolamine-hydrochloric acid buffer (pH 9.5), 0.075M Tris-acetic acid buffer (pH 9.3) etc. may used as the equilibration buffer, and known suitable buffer systems e.g. 1% (v/v) Pharmalyte (pH 3–10.5)-5.2% (v/v) Polybuffer 96-hydrochloric acid buffer (pH 7.0–8.0), 10% (v/v) Polybuffer 96-hydrochloric acid buffer (pH 6.0–7.0), 10% (v/v) Polybuffer 96-acetic acid buffer (pH 6.0–7.0) etc. may be used as the elution buffer. The usual conditions for the FPLC are:

Protein amount: 0.1–10 mg per column
Flow rate: 1–50 ml/h, preferably 10–30 ml/h.

In the chromato focusing technique, PBE 118 (Pharmacia, Sweden), PBE 94 (Pharmacia, Sweden), which are on the market, etc. are used as the gel, and 0.025M triethylamine- hydrochloric acid buffer (pH 11.0), 0.025M diethanolamine- hydrochloric acid buffer (pH 9.4), 0.025M diethanolamine- acetic acid buffer (pH 9.4) etc. as the equilibration buffer, 2.2% (v/v) Pharmalyte (8–10.5)hydrochloric acid buffer (pH 7.0–8.0), 10% (v/v) Polybuffer 96-hydrochloric acid buffer (pH 7.0–8.0), 10%(v/v) Polybuffer 96-acetic acid buffer (pH 6.0–7.0) etc. as the elution buffer. The conditions suitable for the chromato focusing are:

Capacity of column bed: 0.01–10 l per g protein, preferably 100–1,1000 ml
Flow rate: SV=0.01–10, preferably SV=0.1–1.0
Column temperature: 0°–30° C. preferably 2°–5° C.

In accordance with the separation method of the present invention, a protein and a Met-protein are isolated from each other according to the difference of their isoelectric point by putting them into electrophoresis in an electric field or by attaching them to charged carrier packed in a column and eluting them from the carrier by producing a pH-gradiented column in turn. Their separation can be achieved also by applying isocratic elution, where neither pH gradient nor salt concentration gradient is particularly made.

If desired, the protein which has been separated from the Met-protein (e.g. its N-Met analog) in accordance with the methods of the present invention can be further purified by conventional or known methods, to provide a substantially pure protein. Similarly, the Met-protein which has been separated from the protein in accordance with the methods of the present invention can be further purified by conventional or known methods, to provide a substantially pure Met-protein.

For this purpose, the techniques per se known, such as salting-out, hydrophobic chromatography, gel filtration, ion exchange chromatography, and high performance liquid chromatography, which, are commonly used for protein purification, can be properly applied in combination.

The present invention makes it possible for the first time to separate proteins produced by recombinant DNA procedures from their corresponding Met-proteins, so that the proteins are substantially free of their corresponding Met-proteins, e.g., their N-Met analogs. Preferably the proteins produced in accordance with the present invention contain no more than about 3% by weight of their corresponding Met-proteins more preferably not more than 2%, most preferably not more than 1% by weight.

Similarly, the present invention makes it possible for the first time to separate Met-proteins produced by recombinant DNA procedures from their corresponding proteins, so that the Met-proteins are substantially free of their corresponding proteins. Preferably the Met-proteins produced in accordance with the present invention contain no more than about 3% by weight of their corresponding proteins, more preferably not more than 2%, most preferably not more than 1% by weight.

No success has been reported till now where Met-IL-2 or Met-IFN-αA was isolated as a protein. The present invention provides highly purified Met-IL-2 protein and Met-IFN-αA protein for the first time.

Both the proteins and Met-proteins produced according to this invention have a biological or immunological activity similar to the corresponding natural proteins, and they are so highly refined that very few or no impure proteins and pyrogens are contained; therefore, they can be safely used for preparing injections etc.

IL-2 and Met-IL-2 obtained in accordance with the invention both have an activity of promoting the growth of normal T cells or natural killer cells while maintaining their functions. Therefore, IL-2 and Met-IL-2 can be used in growing and subculturing T cells or natural killer cells in vitro for a long period of time or cloning the same. Moreover, this property can be utilized in human IL-2 activity measurement.

Furthermore, IL-2 and Met-IL-2 obtainable by the invention make it possible to selectively grow antigen-specific killer T cells, which recognize and destruct tumor antigens, or natural killer cells, which are capable of killing tumor cells irrespective of the presence or absence of an experience of antigenic sensitization, in vitro. When inoculated into a living organism simultaneously with the introduction of said killer cells into the living organism, IL-2 or Met-IL-2 obtainable by the present invention increases the anti-tumor effect of killer T cells. Therefore, they can be used for the prevention or treatment of tumors or the treatment of immunodeficiency diseases in warm-blooded animals (e.g. mouse, rat, rabbit, dog, cat, pig, horse, sheep, cattle, human).

IL-2 and Met-IL-2 obtained according to the invention are highly purified products and have little antigenicity for humans and are low in toxicity.

As an agent for the prevention and treatment of tumors, IL-2 or Met-IL-2 obtained according to the invention can be administered either parenterally or orally in the form of, for example, injections or capsules prepared by appropriate blending or dilution with a per se known carrier. They can be used either alone or in combination with killer T cells or natural killer cells grown in vitro, as mentioned hereinbefore.

IL-2 and Met-IL-2 produced according to a preferred embodiment of the invention have substantially the same biological activity as the natural human IL-2 and accordingly can be used in the same manner as said natural one. Their dissociation constant in relation to the IL-2 receptor of the responding cells are very small, so that a very small dose is sufficient in most cases.

For the purpose of growing T cells in vitro, IL-2 or Met-IL-2 of the invention can be added to the medium in a concentration of about 0.01–1 U/ml, preferably about 0.1–0.5 U/ml.

The measurement of the bioactivity of interleukin-2 was performed in accordance with the method using interleukin-2 depending cells [Biochem. Biophys. Res. Commun., 109, 363 (1982)].

In an example of the use for the purpose of growing T cells in vitro, IL-2 or Met-IL-2 of the invention is added, to a concentration of 0.1–0.5 unit/ml, to a cell suspension containing, for example, alloantigen-sensitized T cells obtained by 3-day mixed lymphocyte culture of human peripheral blood-derived T cells ($1 \times 10^6$ cells/ml), with B cell transformants ($1 \times 10^6$ cells/ml) resulting from X ray irradiation (1,500 rads) added, in RPMI 1640 medium containing 20% fetal bovine serum. Cultivation is continued for about 1 month while repeating medium exchange at about one-week intervals.

Both the IFN-αA and Met-IFN-αA obtained by means of the present invention have an activity which acts on cells to put them into the anti-virus state. By using this character, the activity of human IFN-αA can be measured.

Furthermore, the IFN-αA and Met-IFN-αA obtained by means of this invention have not only the anti-virus action but also actions, such as cell growth inhibiting action, antibody production inhibiting action, and natural killer activity promoting action.

Each of the IFN-αA and Met-IFN-αA obtained by means of this invention has no antigenicity due to impure proteins and thus they are of low toxicity.

In order to use the IFN-αA or Met-IFN-αA obtained by means of this invention as a therapeutic medicine, the said substance can be orally or parenterally administered as injections, capsules etc., for example, after it is mixed and diluted with a conventional carrier. Daily doses range from $1 \times 10^6$ to $1 \times 10^8$ units, preferably from $5 \times 10^7$ to $6 \times 10^7$ units.

In the cases where an amino acid is indicated by an abbreviation in Claims and Drawings of the present specification, the abbreviations on the basis of IUPAC-IUB Commission on Biochemical Nomenclature of those used commonly in the relating field are used. The examples are shown in the following list. In the case where optical isomers can exist in an amino acid, L-types are indicated as far as not specified.

Gly: Glycine
Ala: Alanine
Val: Valine
Leu: Leucine
Ile: Isoleucine
Ser: Serine
Thr: Threonine
Cys: Cysteine
½ Cys: Half cystine
CmCys: Carboxymethylcysteine
Met: Methionine
Glu: Glutamic acid
Asp: Aspartic acid
Lys: Lysine
Arg: Arginine
His: Histidine
Phe: Phenylalanine
Tyr: Tyrosine
Trp: Tryptophan
Pro: Proline
Asn: Asparagine
Gln: Glutamine
Asp/Asn: Aspartic acid and Asparagine
Glu/Gln: Glutamic acid and Glutamine

EXAMPLES

In the Examples and Reference Examples shown in the following, the present invention is described still more concretely; however, this does not mean that the scope of the present invention is limited to them.

The transformant, *Escherichia coli* DH1/pTF4, disclosed in the Reference Examples, was deposited at Institute for Fermentation, Osaka, Japan (IFO), under IFO-14299, and on Apr. 6, 1984 at Fermentation Research Institute, Agency of Industrial Science and Technology, Ministry of International Trade and Industry, Japan (FRI), under the accession number of FERM P-7578, the latter deposit being converted to a deposit under the Budapest Treaty, has been stored at FRI under the accession number of FERM BP-628.

The transformant, *Escherichia coli* N4830/pTB285, was deposited at IFO under IFO-14437, and on Apr. 30, 1985 at FRI under the accession number of FERM P-8199, the latter deposit being converted to a deposit under the Budapest Teaty, has been stored at FRI under the accession number of FERM BP-852.

EXAMPLE 1

Isolation of IL-2 and Met-IL-2- by Means of FPLC

Figure 3:
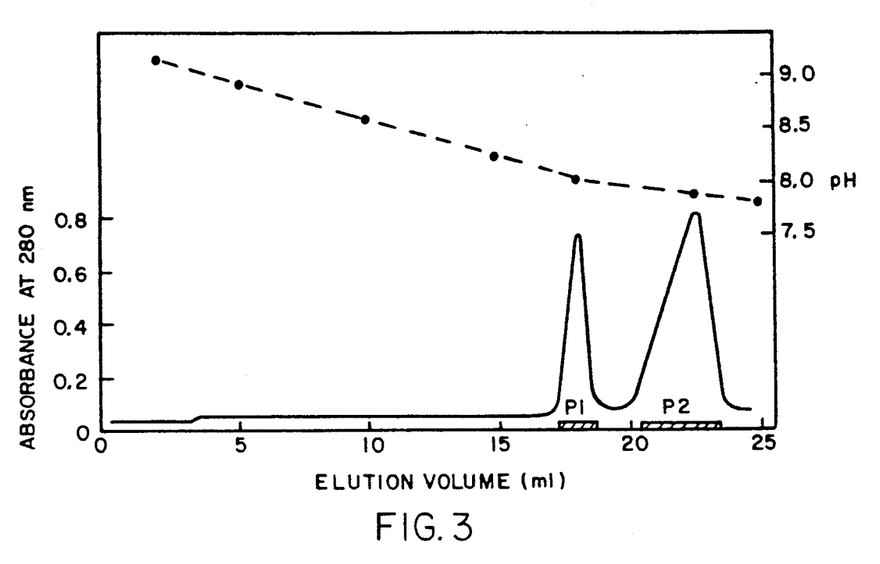
FIG. 3 show the results of the FPLC performed in EXAMPLE 1.

Five ml of 0.005M ammonium acetate buffer (pH 5.0) containing 5.9 mg of the non-glycosylated human interleukin- 2 (protein concentration 1.18 mg/ml), which had been Reference Example 1 (iv) and is a mixture of IL-2 and Met-IL-2, was passed through the Mono-P column for FPLC (0.5×20 cm, Pharmacia) which had been equilibrated with 0.025M diethanolamine-hydrochloric acid buffer (pH 9.4). Then, by using 1% (v/v) Pharmalyte (8-10.5)-5.2% (v/v) Polybuffer 96-hydrochloric acid buffer (pH 8.0), the protein which had been adsorbed to the Mono-P column was eluted. The FPLC operation was performed at the room temperature, the flow rate being 30 ml/h. As a result, peak 1, which is eluted at pH 8.0, and peak 2, which is eluted at pH 7.9, were isolated as shown in FIG. 3. Then, after collected separately, they were subjected to high performance liquid chromatography, where trifluoroacetic acid-acetonitrile was used as the eluting solvent, in order to remove the Polybuffer which had been used in the FPLC operation.

Column: Ultrapore RPSC (1.0×25 cm, Altex, U.S.A.)
Column temperature: 30° C.
Elution solvent A: 0.1% trifluoroacetic acid-99.9% water
Elution solvent B: 0.1% trifluoroacetic acid-99.9% acetonitrile
Flow program: 0 min. (55% A+45%B)-4 min. (55% A+45% B)-28 min.
(42% A+58% B)-38 min.
(34% A+66% B)-43 min.
(20% A+80% B)-44 min.
(55% A+45% B)
Eluting rate: 3.0 ml/min.

Each of the solutions which had been obtained from this chromatography was subjected to freeze-drying and white powder was obtained. The powder from peak 1 in FPLC and that from peak 2 were designated as P1 and P2, respectively. The yield of P1 was 1.12 mg (19.0%) and that of P2 was 3.01 mg (51.0%).

Next, P1 and P2 were subjected to proteochemical analysis. The amino terminal amino acid sequences of P1 and P2 were determined, where 45 μg (3 nmol) of each of them was supplied, in accordance with the automatic Edman procedure with a gas-phase protein sequencer (Applied Biosystem Inc., U.S.A., 470A Type). Phenylthiohydantoin amino acids (PTH-amino acids) were identified by means of high performance liquid chromatography, where Micropack SP-C18 columns (Varian Associates, U.S.A.) were used. The PTH-amino acids which were detected in each stage are shown in Table 1.

TABLE 1

| Cycle | Detected PTH-amino Acids (pmol) | | | |
|---|---|---|---|---|
| | P1 | | P2 | |
| 1 | Ala (2330) | Met (21) | Ala (56) | Met (2600) |
| 2 | Pro (1670) | Ala (77) | Pro (33) | Ala (2430) |
| 3 | Thr (819) | Pro (51) | Thr (45) | Pro (1770) |
| 4 | Ser (222) | Thr (40) | Ser (16) | Thr (789) |

Figure 1:
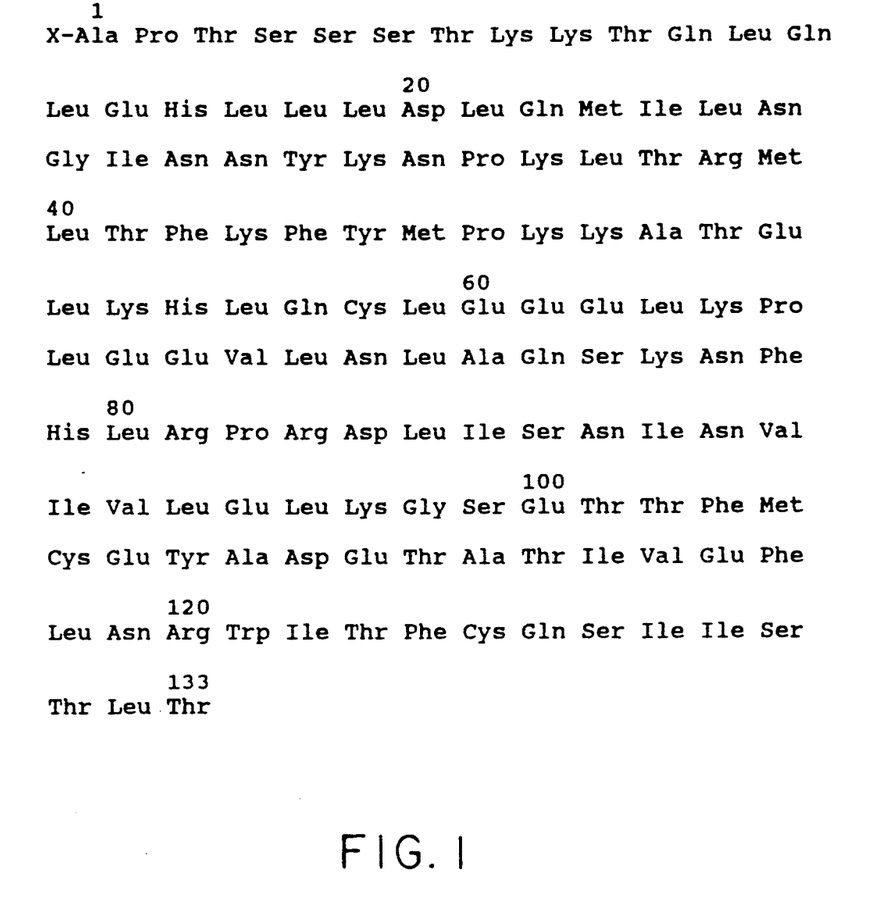
FIG. 1 shows the amino acid sequence of the non-glycosylated human Interleukin-2 protein which has been obtained in reference Example 1 (X represents a hydrogen atom or a methionine residue).

Analysis of carboxyl-terminal amino acids was performed in the following procedure. That is, each of P1 and P2 was put into a glass tube for hydrazine decomposition. Anhydrous hydrazine was used for the experiments. Then, the glass tubes were sealed in vaccuo and heated at 100° C. for 6 hours. After the hydrazine-decomposed matter was treated with benzaldehyde, free amino acids were detected by means of an amino acid analyzer (835 Type, Hitachi). As a result, only threonine was detected for both P1 and P2; their recovery rates being 34.8% and 34.0%, respectively. Therefore, the carboxyl-terminal amino acid of P1 and P2 was identified as threonine. In order to analyze the amino acid composition, constant-boiling hydrochloric acid containing 4% thioglycoli acid was added and the glass tubes were sealed in vaccuo, and then they were subjected to hydrolyses at 110° C. for 24, 48, and 72 hours. The analyses were performed by means of an amino acid analyzer (835 Type, Hitachi). Cystine and cysteine, after oxidized with performic acid, were quantitated as cysteinic acid by means of an amino acid analyzer. The amino acid analysis values were calculated by averaging the values which had been obtained from the hydrolyses for 24, 48, and 72 hours, where the values for serine and threonine were determined by extrapolating the hydrolysis time as 0 hour. The results are shown in Table 2. On the basis of the results of the amino-terminal amino acid sequencing and amino acid composition analysis, it was exemplified that P1 contains the molecular species which is indicated in FIG. 1 as X=a hydrogen atom (IL-2), and that P2 contains the molecular species which is indicated in FIG. 1 as X=a methionine residue (Met-IL-2), of a purity of more than 98% and 99%, respectively.

TABLE 2

| | Composition ratio | | |
|---|---|---|---|
| Amino acid | P1 | P2 | Value deduced from cDNA base sequence |
| Asp/Asn | 11.8 | 11.8 | 12 |
| Thr | 12.6 | 12.6 | 13 |
| Ser | 7.5 | 7.5 | 8 |
| Glu/Gln | 18.6 | 18.7 | 18 |
| Pro | 5.3 | 5.3 | 5 |
| Gly | 2.2 | 2.2 | 2 |
| Ala | 4.9 | 5.0 | 5 |
| ½ Cys | 2.6 | 2.8 | 3 |
| Val | 4.1 | 4.1 | 4 |
| Met | 4.1 | 5.1 | 4 |
| Ile | 8.6 | 8.6 | 9 |
| Leu | 21.8 | 21.9 | 22 |
| Tyr | 3.1 | 3.2 | 3 |
| Phe | 6.0 | 6.1 | 6 |
| Lys | 11.9 | 11.9 | 11 |
| His | 3.0 | 3.0 | 3 |
| Arg | 4.2 | 4.2 | 4 |
| Trp | 1.1 | 1.1 | 1 |

Figure 4:
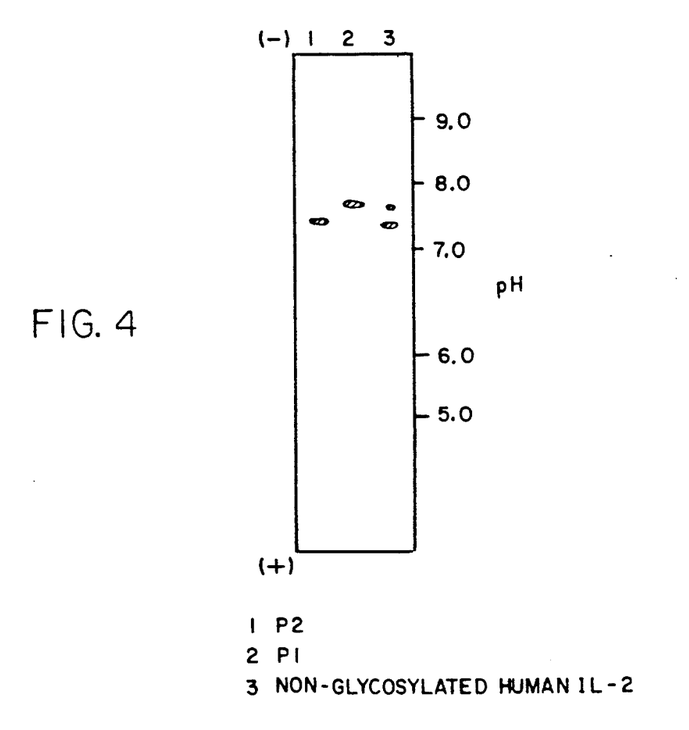
FIG. 4 shows the results of the isoelectric electrophoresis performed in Example 1.

Next, the results of the measurement of the isoelectric points of P1 and P2, which was performed by using Ampholine PAG plates (LKB Co.), are shown in FIG. 4. Nonglycosylated human interleukin-2, which is a mixture of the two raw materials, i.e. IL-2 and Met-IL-2, showed two bands when it was subjected to isoelectric electrophoresis. On the other hand, each of P1 and P2, which had been obtained in the present example, showed one band of which migration distance was different from each other. By measuring the pH values of the PAG plate pieces after the electrophoresis, the isoelectric points were determined as 7.7 and 7.5 for P1 (IL-2) and P2 (Met-IL-2), respectively.

Furthermore, P2 was subjected to trypsin digestion in the following procedure and a peptide map was obtained. That is, 1.25 μg of TPCK-trypsine (Worthington Co., USA) was added to 100 μl of 0.02M sodium bicarbonate solution (pH 8.0) containing 50 μg of P2, and they were kept in a reaction at 37° C. for 28 hours.

Figure 5:
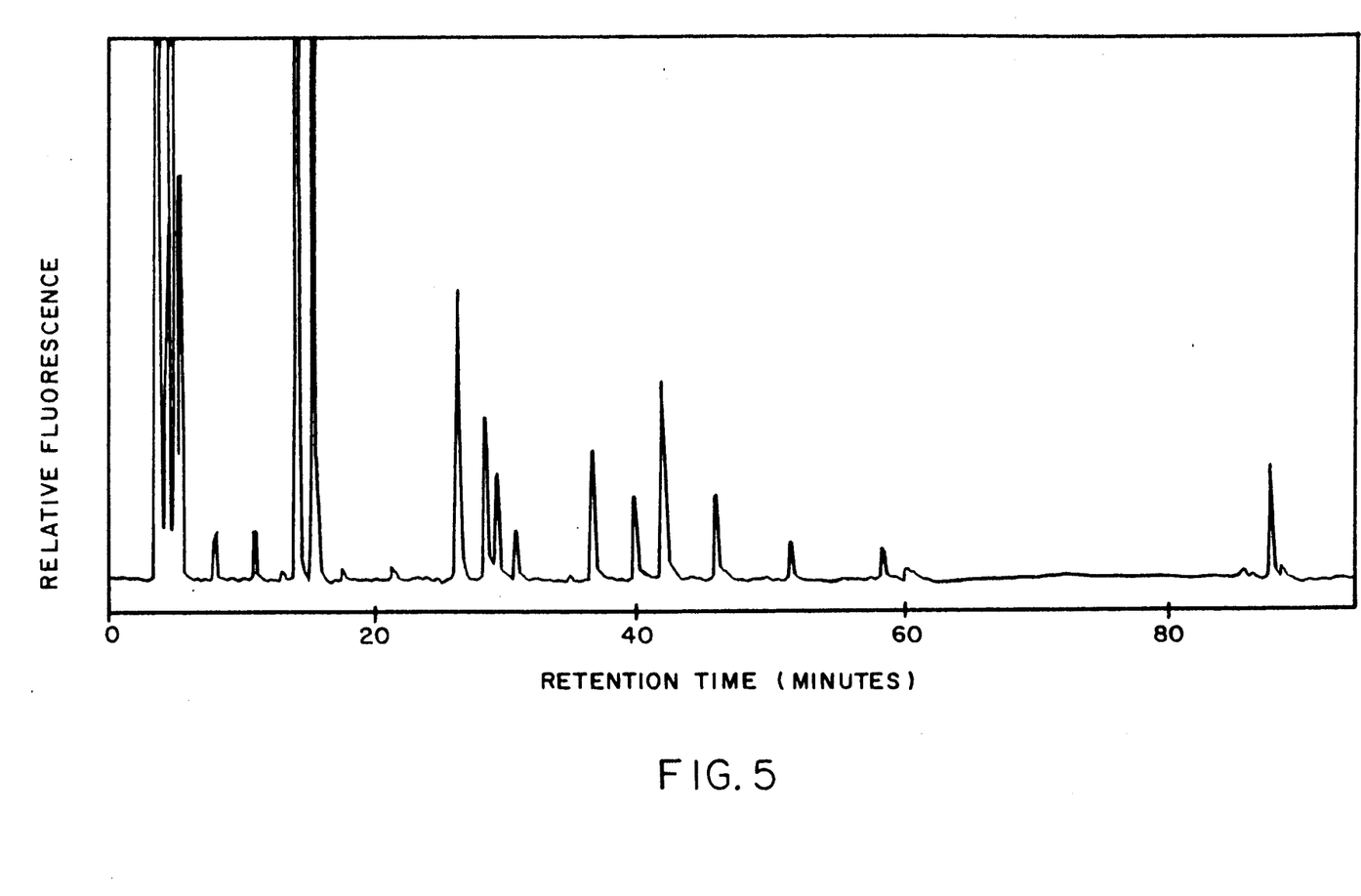
FIG. 5 shows the results of the trypsin digestion performed in Example 1.

The reaction was stopped by adding 400 μl of 1% (v/v) trifluoroacetic acid to the reacting solution. The digestive solution obtained was subjected to high performance liquid chromatography under the following conditions and the map shown in FIG. 5 was obtained.

High performance liquid chromatography: 5040 Type, Varian Associates, USA

Column: Nucleosyl 5C18 (Machelehner Gel AG, West Germany)

Column temperature: 30° C.

Elution solvent A: 0.1% trifluoroacetic acid-99.9% water (v/v)

Elution solvent B: 0.1% trifluoroacetic acid-99.9% acetonitrile (v/v)

Flow program: 0 min. (85% A+15% B)—15 min. (72% A+28% B)—16 min.
(64% A+36% B)—80 min.
(40% A+60% B)—85 min.
(15% A+85% B)

Eluting rate: 3.0 ml/min.

Detection method: Post-labelling in accordance with the orthophthalaldehyde method [Anal., Chem., 43, 880 (1971)]

EXAMPLE 2

Isolation of IL-2 and Met-II-2 by means of Chromato Focusing

Figure 6:
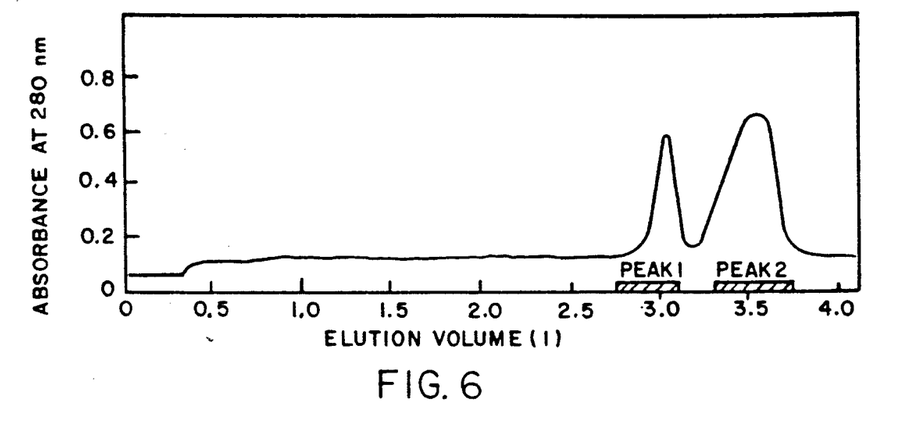
FIG. 6 shows the results of the chromato focusing performed in Example 2.

A quantity of 500 ml of 0.05M ammonium acetate buffer (pH 5.0) containing 545 mg of the non-glycosylated human interleukin-2 (protein concentration 1.09 mg/ml) which had been obtained in Reference Example 1 (iv) and which is a mixture of IL-2 and Met-IL-2, was passed through a column (2.7×87 cm) packed with the PBE94 (Pharmacia) which had been equilibrated with 0.025M diethanolamine-hydrochloric acid buffer (pH 9.4). Then, chromato focusing was performed by using 1% (v/v) Pharmalyte (8–10.5)-5.2% (v/v) Polybuffer 96-hydrochloric acid buffer (pH 8.0) as the eluate. The operation was done under the following conditions: temperature 4° C., flow rate 200 ml/h. As a result, Peak 1, which is eluted at pH 8.5, and Peak 2, eluted pH 8.3, were isolated as shown in FIG. 6. After Polybuffer was removed with the same method as shown in Example 1, the yields of protein were 9.4 mg (17.4%) and 336 mg (61.6%) for Peak 1 and Peak 2, respectively. Amino-terminal amino acid analysis was performed by detecting the dansyl amino acids which had been produced by hydrolyzing Peak 1 and Peak 2 with hydrochloric acid after dansylization, by means of high performance liquid chromatography, where Micropack SP columns were used. As a result, it was exemplified that Peak 1 contains IL-2 of a purity of more than 99.6% and that Peak 2 does met-IL-2 of a purity of more than 99.5%.

EXAMPLE 3

Isolation of IL-2 and Met-IL-2 by Means of DEAE-Toyopearl Ion Exchange Chromatography In order to adjust the pH value to 8.5, 10 ml of 10 mM Tris-hydrochloric acid buffer (pH 9.0) to 10 ml of 0.005M ammonium acetate buffer (pH 5.0) containing 10.3 mg of the non-glycosylated human interleukin-2 (protein concentration 1.03 mg/ml) which had been obtained in Reference Example 1 (iv) and which is a mixture of IL-2 and Met-IL-2. Then, the combined solution was passed through a column (1.0×64 cm) packed with the DEAE-Toyopearl 650M (Toyo Soda Manufacturing Co.) which had been equilibrated with 10mM Tris-hydrochloric acid buffer (pH 8.5) and it was subjected to pH gradient elution, where 1 l of 10mM Tris-hydrochloric acid buffer (pH 8.5) and 1 l of 10mM Tris-hydrochloric acid buffer (pH 7.0) were used. The operation was done under the following conditions: temperature 4° C., flow rate 100 ml/h. As a result, two peaks (Peak 1 and Peak 2) were detected, although the resolution was poorer than those for FPLC and chromate focusing. In order to prevent the peaks from overlapping with each other, the first half of Peak 1 and the last half of Peak 2 were collected separately. The yields were 0.82 mg (8.0%) and 1.98 mg (19.2%) for Peak 1 and Peak 2, respectively. As a result of the amino-terminal amino acid analysis by means of the dansyl method, it was exemplified that Peak 1 contains IL-2 of a purity of more than 90% and that Peak 2 does Met-IL-2 of a purity of more than 95%.

EXAMPLE 4

Isolation of IL-2 and Met-IL-2 by Means of FPLC 5 ml of the partially-purified solution of the non-glycosylated human interleukin-2 which had been obtained in Reference Example 1 (iii), which contains IL-2 and Met-IL-2, was passed through the Mono-P column for FPLC (0.5×20 cm, Pharmacia) which had been equilibrated with 0.025M diethanolamine-hydrochloric acid buffer (pH 9.4). Then, the proteins which were adsorbed to the Mono-P column was eluted by using 1% (v/v) Pharmalyte (8–10.5)-5.2% (v/v) Polybuffer 96-hydrochloric acid buffer (pH 8.0), where the eluting rate was 25 ml/h and the column temperature was the room temperature. As a result, two fractions were isolated: the fraction containing IL-2 (Peak 1) and that containing Met-IL-2 (Peak 2). The activity yields were 25% and 54% for Peak 1 and Peak 2, respectively.

EXAMPLE 5

Isolation of IL-2 and Met-IL-2 by Means of SP-5PW Column

A quantity of 0.5 ml of 0.05M ammonium acetate buffer (pH 5.0) containing the non-glycosylated human interleukin-2 (protein concentration 1.03 mg/ml) which had been obtained in Reference Example 2 and which is a mixture of IL-2 and Met-IL-2, was passed through the SP-5PW column for high performance liquid chromatography (0.75×7.5 cm, Toyo Soda Manufacturing Co.) which had been equilibrated with 0.025M phosphate buffer (pH 7.4), and proteins were eluted by using 0.025M phosphate buffer (pH 7.4). The column temperature was 35° C. and the flow rate of the buffer was 0.5 ml/min. As the chromatographic system, a Varian 5500 Type liquid chromatographer was used.

Figure 7:
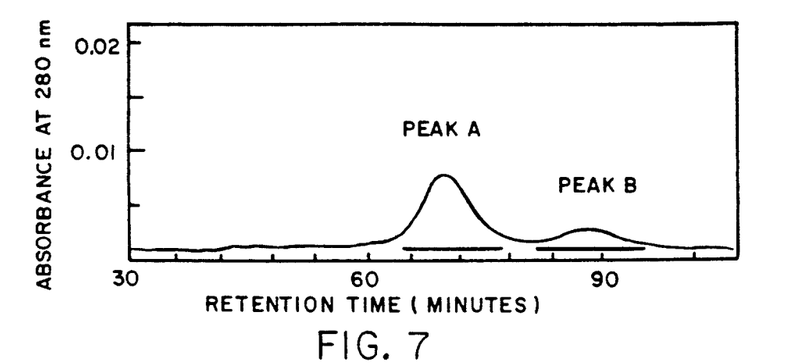
FIG. 7 shows the results of the SP-5PW ion exchange chromatography performed in Example 5.

As a result, the non-glycosylated interleukin-2 was eluted as two peaks (Peak A and Peak B), as shown in FIG. 7. Each of the peaks was collected separately (in the figure, indicated as ■) and they were subjected to amino-terminal amino acid analysis. Then, it was exemplified that Peak A and Peak B contain more than 99.5% of Met-IL-2 and IL-2, respectively.

EXAMPLE 6

Isolation of IFN-αA and Met-IFN-αA by Means of FPLC

Figure 8:
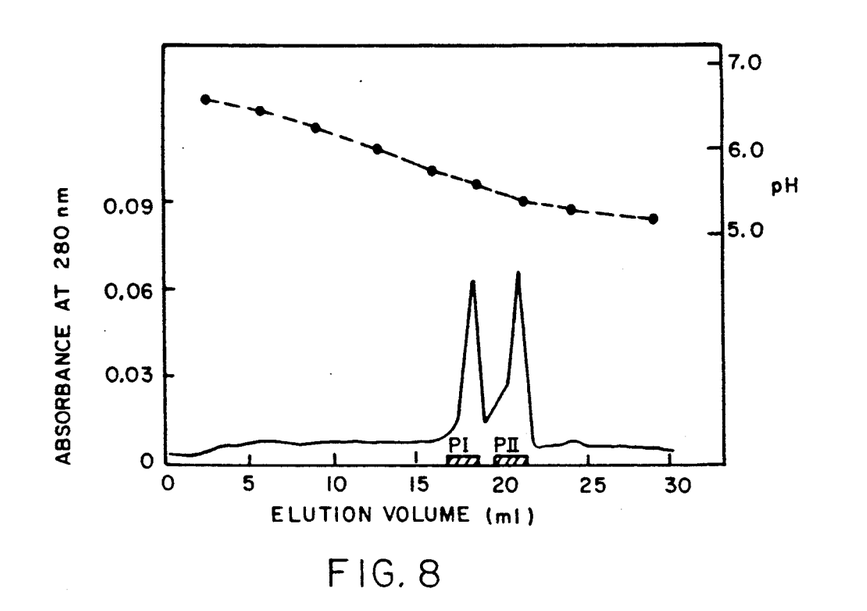
FIG. 8 shows the results of the FPLC performed in Example 6.

A quantity of 1.0 ml of 0.12M sodium chloride-0.025M ammonium acetate buffer (pH 5.0) containing 2.96 mg of the non-glycosylated human interferon-αA (protein concentration 2.96 mg/ml) which had been obtained by means of the method described in Reference Example 3 and which is a mixture of IFN-αA and Met-IFN-αA, was subjected to desalting by passing it through the PD-10 column (1.5×5 cm, Pharmacia) which had been equilibrated with 0.025M imidazole-hydrochloric acid buffer (pH 6.7). A quantity of 1.5 ml of the eluate containing 2.37 mg of the non-glycosylated human interferon-αA (protein concentration 1.58 mg/ml) obtained as above, was passed through the Mono-P column for FPLC (0.5×20 cm, Pharmacia) which had been equilibrated with 0.025M imidazole-hydrochloric acid buffer (pH 6.7). Then, the proteins which had been adsorbed to the Mono-P column were eluted by using 10% (v/v) Polybuffer 74-hydrochloric acid buffer (pH 5.5). The FPLC operation was performed at the room temperature: the flow rate being 30 ml/h. As a result, Peak I, which is eluted at pH 5.6, and Peak II, which is eluted at pH 5.4, were isolated, as shown in FIG. 8. In order to remove the Polybuffer which was used in the FPLC, the two peaks, after collected separately, were subjected to high performance liquid chromatography, where a mixture of trifluoroacetic acid and acetonitrile was used as the elution solvent.

Column: Ultrapore RPSC (1.0×25 cm, Altex, U.S.A.)
Column temperature: 30° C.
Elution solvent A: 0.1% trifluoroacetic acid-99.9% water
Elution solvent B: 0.1% trifluoroacetic acid-99.9% acetonitrile
Elution program: 0 min. (60% A+40% B)—45min. (45% A+55% B)—46 min. (60% A+40% B)
Flow rate: 3.0 ml/min.

Each of the solutions obtained by means of the said chromatography was subjected to freeze-drying and white powder was obtained. The powder obtained from Peak I and that from Peak II were designated as PI and PII, respectively. The yield of PI was 0.723 mg (24.4%) and that of PII was 0.945 mg (31.9%).

Next, PI and PII were subjected to proteochemical analysis. After PI and PII were reduced and carboxymethylated, their amino-terminal amino acid sequences were determined by means of the automatic Edman procedure, with a gasphase protein sequencer (470A Type, Applied Biosystems Inc.), where 40 μg (2.1 nmol) of each of them was used. Phenylthiohydantoin amino acids (PTH-amino acids) were identified by means of high performance liquid chromatography, where a Micropack SP-C18 column (Varian Associates) was used. The PTH-amino acids which were detected in each step are shown in Table 3.

TABLE 3

| Cycle | Detected PTH-amino Acids (pmol) | | | |
|---|---|---|---|---|
| | PI | | PII | |
| 1 | CmCys (28) | Met (1630) | CmCys (1370) | Met (15) |
| 2 | Asp (20) | CmCys (1250) | Asp (1220) | CmCys (21) |
| 3 | Leu (22) | Asp (986) | Leu (1170) | Asp (11) |
| 4 | Pro (14) | Leu (963) | Pro (761) | Leu (8) |

As a result of the carboxyl-terminal amino acid analysis which was performed in the same manner as in Example 1, only glutamic acid was detected from PI and PII: the recovery rates being 12.5% and 14.3%, respectively.

Figure 2:
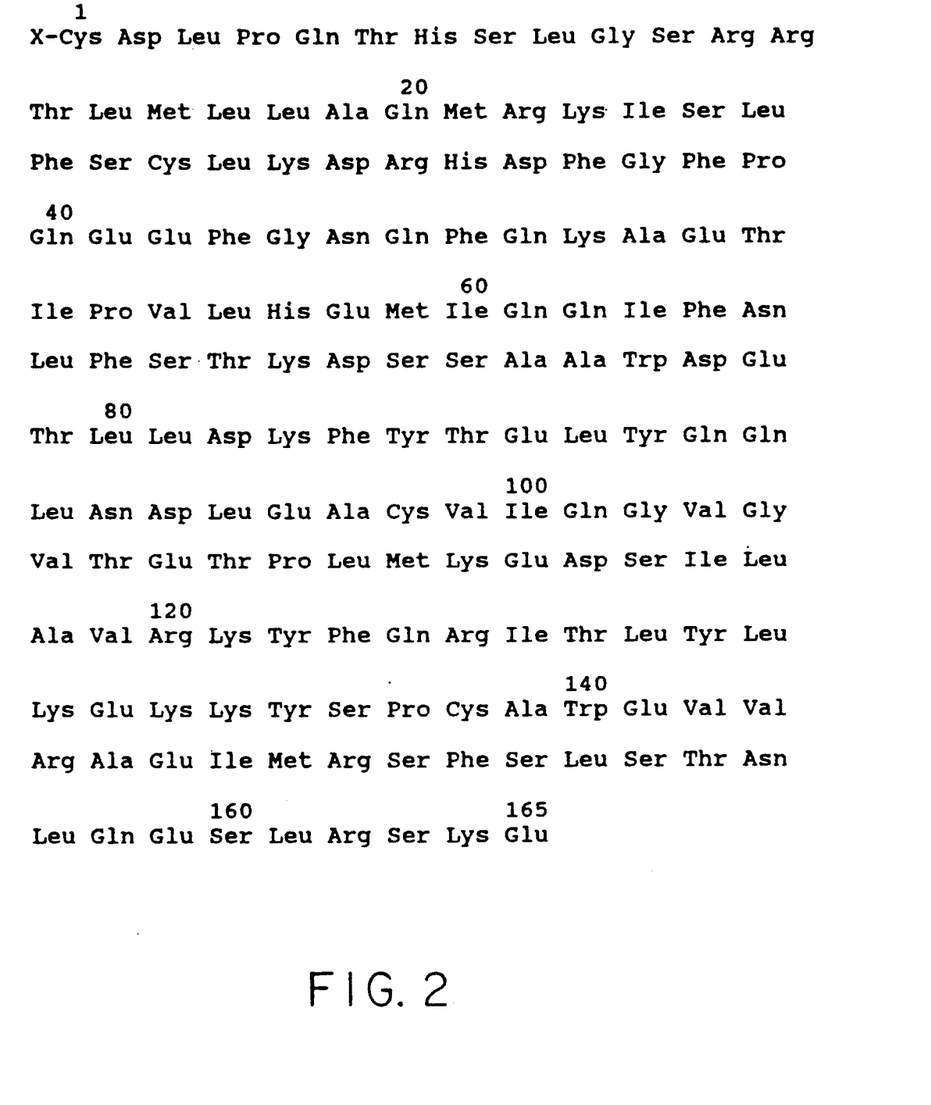
FIG. 2 shows the amino acid sequence of the non-glycosylated human interferon-α A protein which has been obtained in reference Example 3 (X represents a hydrogen atom or a methionine residue).

Table 4 shows the results obtained from the amino acid composition analysis which was performed in the same manner as in Example 1. On the basis of the results of the amino-terminal amino acid sequencing and amino acid composition analysis, it was exemplified that PI and PII contain the molecule species (Met-IFN-αA) which is indicated in FIG. 2 as X=a methionine residue and that (IFN-αA) indicated in FIG. 2 as X=a hydrogen atom, respectively, of a purity of more than 98%.

TABLE 4

| | Composition ratio | | |
|---|---|---|---|
| Amino acid | PI | PII | Value deduced from cDNA base sequence |
| Asp/Asn | 12.0 | 12.0 | 12 |
| Thr | 9.7 | 9.7 | 10 |
| Ser | 12.9 | 12.5 | 14 |
| Glu/Gln | 26.1 | 26.0 | 26 |
| Pro | 5.0 | 4.9 | 5 |
| Gly | 4.9 | 4.9 | 5 |
| Ala | 8.1 | 8.1 | 8 |
| ½ Cys | 3.8 | 3.9 | 4 |
| Val | 7.1 | 7.1 | 7 |
| Met | 6.1 | 5.1 | 5 |
| Ile | 7.9 | 7.8 | 8 |
| Leu | 20.8 | 20.6 | 21 |
| Tyr | 5.2 | 5.1 | 5 |
| Phe | 9.9 | 9.8 | 10 |
| Lys | 11.0 | 11.1 | 11 |
| His | 3.5 | 3.4 | 3 |
| Arg | 8.8 | 8.8 | 9 |
| Trp | 2.2 | 2.1 | 2 |

The isoelectric points of PI and PII were measured by using Ampholine PAG plates (LKB Co.), and then the isoelectric point of PI (Met-IFN-αA) was calculated as 6.3 and that of PII (IFN-αA) as 6.2.

EXAMPLE 7

IL-2 Preparation for Injection

The solution containing IL-2, obtained in Example 1, after adsorbed under the aseptic condition to the CM Toyopearl (Toyo Soda Manufacturing Co.) which has been equilibrated with 0.025M ammonium acetate buffer (pH 5.0), is eluted with the said buffer containing 0.15M NaCl. The eluate is diluted by adding 0.15M NaCl properly and HSA is so added that its concentration is 0.5 percent. Then, the eluted solution is filtered with a membrane filter (pore size 0.22 μm). The filtrate obtained is aseptically collected into vials separately (1 ml per vial) and freeze-dried to prepare IL-2 for injection. This preparation for injection will be reconstituted with 1 ml of distilled water for injection, when used.

EXAMPLE 8

IFN-αA Preparation for Injection

The solution containing IFN-αA, obtained in Example 6, after adsorbed under the aseptic condition to a column packed with the CM-Toyopearl (Toyo Soda Manufacturing Co.) which has been equilibrated with 0.025M ammonium acetate buffer (pH 5.0), is eluted with the said buffer containing 0.15M NaCl. The eluate is diluted by adding 0.15M NaCl properly and HSA is added to 0.5 percent. Then, the eluted solution is filtrated with a membrane filter (pore size 0.22 μm). The filtrate obtained is aseptically collected into vials separately (1 ml per vial) and freeze-dried to prepare IFN- αA for injection. This preparation for injection, when used, is reconstituted with 1 ml of distilled water for injection.

While not presently preferred, the above preparations for injection can also be made using purified Met-IL-2 and purified Met-IFN-αA, in place of the purified IL-2 and IFN-αA described above, respectively.

Reference Example 1

Production of non-glycosylated human IL-2 protein . . . I (i) Cultivation of the transformant The transformant E. coli DH1/pTF4 [refer to the specification of Japanese Patent Application 225079/1983 (filed Nov. 28, 1983) which corresponds to EP Publication (laid open) No. 0145390] was inoculated into 50 ml of a liquid medium (pH 7.0) containing 1% Bacto tryptone (Difco Laboratories, USA), 0.5% Bacto yeast extract (Difco Laboratories, USA), 0.5% sodium chloride and 7 µg/ml tetracycline as placed in a 250-ml erlenmeyer flask. After incubation at 37° C. overnight on a swing rotor, the culture medium was transferred to a 5-liter jar fermenter containing 2.5 liters of M9 medium containing 0.5% casamino acids, 0.5% glucose and 7 µg/ml tetracycline. Incubation was then conducted with aeration and stirring at 37° C. for 4 hours and, after addition of 3-β-indolylacrylic acid (25 µg/ml), for further 4 hours. Cells were harvested from the thus-obtained 2.5-liter culture broth by centrifugation, frozen at −80° C. and stored.

(ii) Extraction

The freeze-stored cells (12.1 g) obtained above were suspended in 100 ml of an extractant (pH 7.0) containing 7M guanidine hydrochloride and 0.1M Tris.HCl, the suspension was stirred at 4° C. for 1 hour and the lysate was centrifuged at 28,000×g for 20 minutes to obtain 92 ml of a supernatant.

(iii) Partial purification of IL-2 protein

The supernatant fluid obtained above was dialyzed against 0.01M Tris.HCl buffer (pH 8.5) and then centrifuged at 19,000×g for 10 minutes to give 94 ml of a dialyzed supernatant fluid. This was applied to a DE 52 (DEAE-cellulose, Whatman, Great Britain) column (50 ml in volume) equilibrated with 0.01 M Tris.HCl buffer (pH 8.5) for protein adsorption. Proteins were eluted with a linear NaCl concentration gradient (0–0.15M NaCl, 1 liter).

(iv) Purification of IL-2 protein

The active fractions (53 ml) were concentrated to 4.8 ml using a YM-5 membrane (Amicon, USA) and subjected to gel filtration using a Sephacryl S-200 (Pharmacia, Sweden) column (500 ml in volume) equilibrated with 0.1M Tris.HCl (pH 8.0)-1M NaCl buffer. The active fractions (28 ml) obtained were concentrated to 2.5 ml using a YM-5 membrane. The concentrate was applied to an Ultrapore RPSC (Altex, USA) column for adsorption, and high performance liquid chromatography was performed using a trifluoroacetic acid-acetonitrile system as the mobile phase.

The conditions used: column, Ultrapore RPSC (4.6×75 mm); column temperature, 30° C.; solvent A, 0.1% trifluoroacetic acid-99.9% water; solvent B, 0.1% trifluoroacetic acid-99.9% acetonitrile; elution program, minute 0 (58% A+32% B)—minute 25 (55% A+45% B)—minute 35 (45% A+55% B)—minute 45 (30% A+70% B)—minute 48 (100% B); elution rate, 0.8 ml/min.; detection wave length, 230 nm. An active fraction was collected at a retention time of about 39 minutes. Thus was obtained 10 ml of a solution containing 0.53 mg of nonglycosylated human IL-2 protein [specific activity, 30,000 U/mg; activity recovery from the starting materials, 30.6%; purity of protein, 99% (determined by densitometry on an SDS-polyacrylamide gel electrophorefogram)].

Lyophilization of the above solution gave a white powder. The powder had a IL-2 specific activity of 26,000 U/mg.

REFERENCE EXAMPLE 2

Production of non-glycosylated human IL-2 protein . . . II (i) Construction of the expression plasmid The plasmid pILOT 135-8 having human IL-2 gene [refer to Example 1 (vii) in the specification of Japanese Patent Application 225079/1983 (filed Nov. 28, 1983) which corresponds to EP Publication (laid open) No. 0145390].

The plasmid pILOT 135-8 obtained in Reference was cleaved with the restriction enzyme HgiAI. The thus obtained 1294 bp DNA fragment was treated with T4 DNA polymerase to have flat ends and was connected with EcoRI linker dTGCCATGAATTCATGGCA by using T4 DNA ligase. The thus-obtained DNA was digested with EcoRI to obtain a DNA fragment which additionally had translational start codon ATG and human IL-2 gene.

Figure 9:
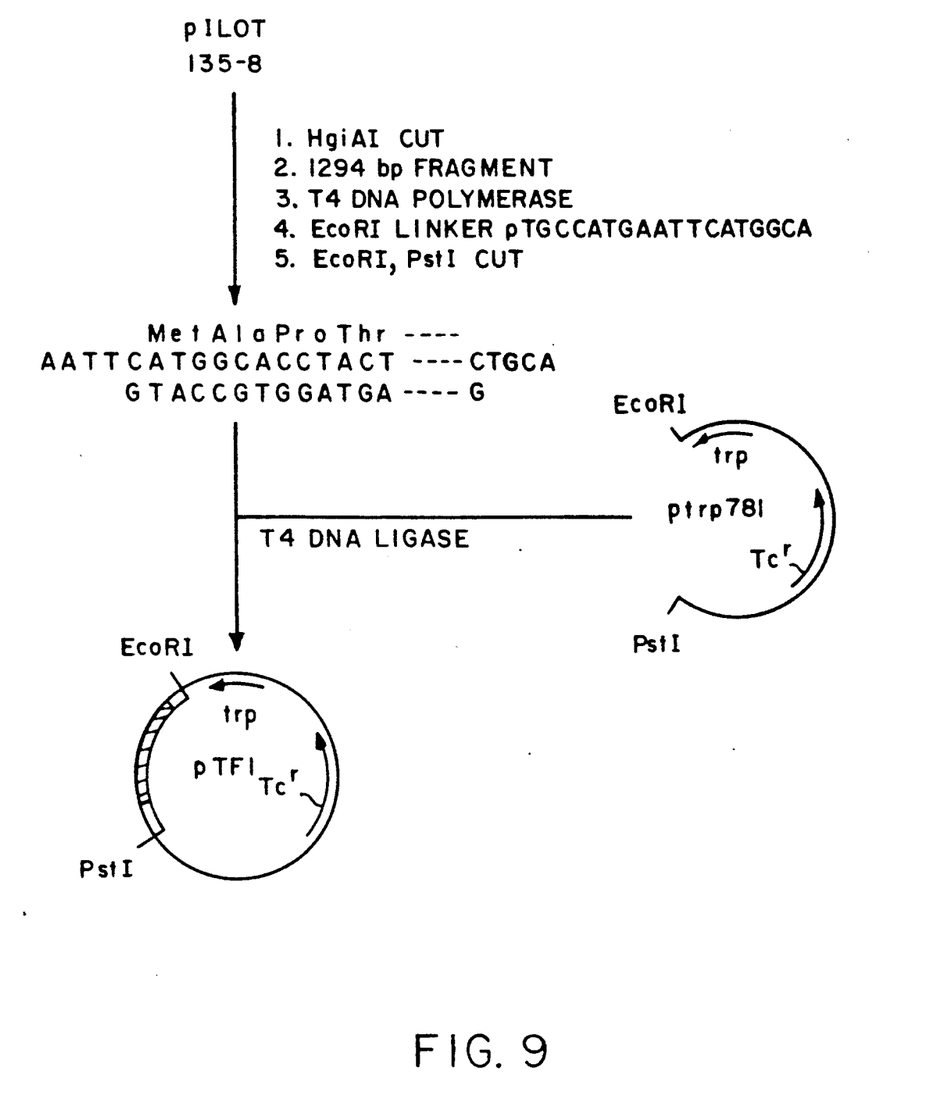
FIG. 9 shows the structural figure of plasmid pTF-1 described in reference Example 2.

This DNA fragment was inserted by using T4 DNA ligase into ptrp 781 (Nucleic Acids Research, 11, 3077 (1983)]which had been digested at the EcoRI-PstI site. The thus obtained expression plasmid pTF 1 had a translational start codon and a human IL-2 gene downstream from the trp promoter (FIG. 9).

Figure 10:
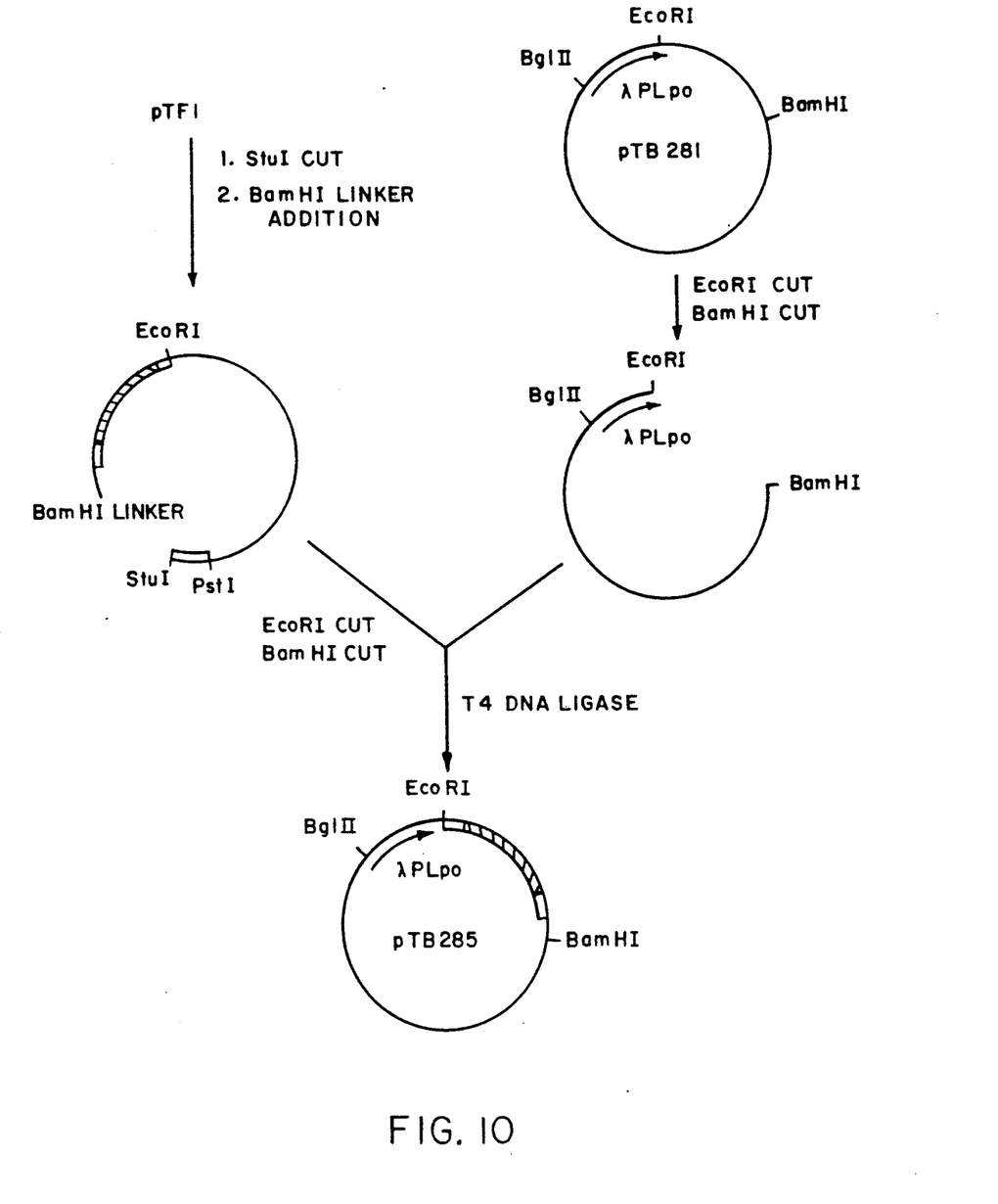
FIG. 10 shows the structural figures of plasmid pTB-285 disclosed in reference Example 2.

The plasmid pTF 1 was cleaved with the restriction enzyme StuI and joined with the BamHI linker. This plasmid DNA was treated with the restriction enzymes BamHI and EcoRI, followed by insertion into pTB 281, which has the λPL promoter at the EcoRI-BamHI site. The expression plasmid thus obtained was named pTB 285 (FIG. 10).

(ii) Production of the transformant

Escherichia coli N4830 was transformed with the plasmid pTB285 obtained above in accordance with the method of Cohen et al. [Pro. Natl. Acad. Sci. U.S.A. 69, 2110 (1972)] to obtain a transformant (Escherichia coli N4830/pTB285) carrying said plasmid.

(iii) Cultivation of the transformant

E. coli N4830/pTB285 was inoculated into 50 ml of a liquid medium (pH 7.0) containing 1% Bacto tryptone (Difco Laboratories, USA), 0.5% Bacto yeast extract (Difco Laboratories, USA), 0.5% sodium chloride and 50 µg/ml ampicillin and placed in a 250-ml erlenmeyer flask. After incubation at 35° C. overnight on a swing rotor, the culture medium was transferred to a 5-liter jar fermenter containing 2.5 liters of M9 medium containing 0.5% casamino acids, 0.5% glucose and 50 µg/ml ampicillin. Incubation was then conducted with aeration and stirring at 35° C. for 4 hours and 42° C. for an additional 3 hours. Cells were harvested from the thus-obtained 2.5-liter culture broth by centrifugation, frozen at −80° C. and stored.

(iv) Extraction

A quantity of 20 g of the freezed cells was suspended uniformly into 100 ml of the extracting solution (pH 7.0) containing 7M guanidine hydrochloride and 0.1M Tris.HCl, and stirred at 4° C. for 4 hours. Then, it was subjected to centrifugation at 28,000×g for 20 minutes to obtain the supernatant.

(v) Partial purification of interluekin-2 protein

The supernatant obtained, after dialyzed against 0.01M Tris.HCl buffer (pH 8.5), was centrifuged at 19,000×g for 10 minutes. The newly obtained supernatant was passed through a column (500 ml) packed with the DE52 (DEAE-cellulose, Wattman, UK) which had been equilibrated with 0.01M Tris.HCl buffer (pH 8.5), to adsorb protein. Then, a NaCl concentration linear gradient (0–0.15M NaCl, 1 l) was made to elute IL-2, and an active fraction was obtained.

(vi) Purification of interleukin-2 protein

The active fraction obtained in the above procedure, after concentrated into 5 ml by using a YM-5 membrane (Amicon Co., USA), was subjected to gel filtration by using a column (500 ml) packed with Sephacryl S-200 (Pharmacia, Sweden) which had been equilibrated with 0.1M Tris.HCl (pH 8.0)-1M NaCl buffer. A quantity of 40 ml of the newly obtained active fraction was concentrated into 3 ml with a YM-5 membrane. The concentrate obtained was adsorbed to a column packed with Ultrapore RPSC (Altex, USA), and then it was subjected to high performance liquid chromatography, where trifluoroacetic acid-acetonitrile was used as the elution solvent. The conditions were:

Column: Ultrapore RPSC (4.6×75 mm)
Column temperature: 30° C.
Elution solvent A: 0.1% trifluoroacetic acid-99.9% water
Elution solvent B: 0.1% trifluoroacetic acid-99.9% acetonitrile
Elution program: 0 min. (68% A+32% B)—25 min. (55% A+45% B)—35 min.
(45% A+55% B)—45 min.
(30% A+70% B)—48 min. (100% B)
Flow rate: 0.8 ml/min.
Detection wave length: 230 nm.

Under these conditions, 10 ml of a mixture of IL-2 and Met-IL-2, which is an active fraction with a retention time of about 39 minutes, was collected.

REFERENCE EXAMPLE 3

Production of non-glycosylated human IFN-αA (i) Cultivation of the transformant

A 5-liter jar fermenter containing 2.5 liters of (1) a medium (nutrient medium) prepared by adding 25 g/liter of glucose, 5 g/liter of Casamino acid (Difco, U.S.A.), 70 mg/liter of vitamin $B_1$ hydrochloride and 5 mg/liter of tetracycline hydrochloride to M-9 medium or (2) a medium (chemically defined medium) prepared by adding 25 g/liter of glucose, 4 g/liter of sodium L-glutamate, 27 mg/liter of $FeCl_3.6H_2O$, 8 mg/liter of $CuSO_4.5H_2O$, , 8 mg/liter of $ZnSO_4.7H_2O$, 70 mg/liter vitamin $B_1$ hydrochloride, 5 mg/liter of tetracycline hydrochloride, 50 mg/liter of L-proline and 50 mg/liter of L-leucine to M-9 medium was inoculated with *Escherichia coli* 294 (ATCC 31446)/pLe IF A trp 25 carrying a plasmid with the structural gene of human leukocyte IFN-αA coding for the amino acid shown in FIG. 2 (Example I of European Patent Application Publication No. 43,980). Cultivation was started at an aeration rate of 2.5 liters/minute, an agitation rate of 1000 rpm and a temperature of 37° C. In the course of cultivation, the temperature was lowered to 33° C. at OD 3000 KU, to 29° C. at OD 5000 KU and to 25° C. at OD 7000 KU. In this manner, the cultivation was continued for 48 hours. The dissolved oxygen concentration was maintained at not less than 5% during the cultivation. When, during cultivation, the glucose ocncentration lowered to 1% or below, glucose was added at a rate of 25 g/liter.

(ii) Extraction

Cells were harvested by centrifugation of 2 liters of the culture broth obtained in (i) and suspended in 100 ml of 50 mM Tris.HCl (pH 7.6) containing 10% sucrose, 0.2M NaCl, 10 mM ethylenediaminetetraacetate (EDTA), 10 mM spermidine, 2 mM phenylmethylsulfonyl fluoride (PMSF) and 0.2 mg/ml lysozyme. The suspension was stirred at 4° C. for an hour, then maintained at 37° C. for 5 mintues, and treated in a sonicator (Altec, USA) at 0° C. for 40 seconds. The lysate was centrifuged at 11,300×g for an hour to give 95 ml of a supernatant.

(iii) Purification of IFN-αA protein

This supernatant (95 ml) was diluted to 300 ml with 20 mM Tris-HCl (pH 7.6) containing 1 mM EDTA and 0.15M NaCl (TEN) and the diluted solution was applied to an anti-IFN-αA antibody column (20 ml).

After washing the column well with TEN, elution was performed with 0.2M acetic acid containing 0.1% Tween 20 (Wako Pure Chemical Industries, Japan). Active fractions were combined, adjusted to pH 4.5 and applied to a CM cellulose column for adsorption. The column was washed well and elution was conducted with 0.025M ammonium acetate buffer (pH 5.0) containing 0.15M NaCl. Again, active fractions were combined and lyophilized to give 320 mg of a human leukocyte IFN-αA powder.

SDS-polyacrylamide gel electrophoresis revealed that this product had a molecular weight of 19000±1000. The antiviral activity of the human leukocyte IFN protein finally obtained here was $2\times10^8$ U/mg. With respect to other physico-chemical properties, amino acid composition and peptide mapping, the product behaved in quite the same manner as recombinant human leukocyte IFN produced in the conventional medium.

What is claimed is:

1. A method of separating a protein or a Met-protein from a mixture comprising the protein and the Met-protein, the Met-protein comprising an amino acid sequence which is sufficiently similar to the amino acid sequence of the first protein to provide a physiological activity provided by the first protein and the Met-protein bearing an additional methionine residue at its amino terminus as compared to the first protein, which comprises subjecting the mixture to a separation procedure utilizing the difference in the isoelectric points between the first protein and the second protein.

2. A method according to claim 1, wherein the separation procedure comprises (a) subjecting the mixture to migration in an electric field or (b) eluting the protein and the Met-protein from a charged carrier in accordance with their respective isoelectric points, by using a pH gradient or a salt concentration gradient in the carrier.

3. A method according to claim 2, wherein the mixture is subjected to migration in an electric field selected from the group consisting of density gradient isoelectric electrophoresis, gel isoelectric electrophoresis and isotachophoresis.

4. A method according to claim 2, wherein the protein and the Met-protein are eluted from a charged carrier selected from the group consisting of chromato focusing, fast protein liquid chromatography, diethylaminoethyl-ion exchange chromatography, carboxymethyl-ion exchange chromatography and sulphopropyl-ion exchange chromatography.

5. The method according to claim 1, wherein the Met-protein comprises the amino acid sequence of the first protein bearing an additional methionine residue at the amino terminus.

6. The method according to claim 1, wherein the Met-protein consists essentially of the amino acid sequence of the first protein bearing an additional methionine residue at the amino terminus.

7. A method according to claim 1, wherein the protein and the Met-protein are produced by gene recombination technology.

8. A method according to claim 1, wherein the protein is selected from the group consisting of a cytokine, a peptide hormone, an antigen protein of a pathogenic microorganism, an enzyme and a hemoprotein.

9. A method according to claim 1, wherein the protein has a molecular weight of about 3,000-50,000.

10. A method according to claim 9, wherein the molecular weight is 5,000-30,000.

11. A method according to claim 1, the protein comprises about 30-500 amino acids.

12. A method according to claim 11, wherein the protein consists of 50-300 amino acids.

13. A method according to claim 1, wherein the protein and the Met-protein have an isoelectric point of about 4 to about 11.

14. A method according to claim 1, wherein the protein and the Met-protein have an isoelectric point of about 5 to about 8.

15. A method according to claim 1, wherein the difference of isoelectric points between the protein and the Met-protein is at least 0.01.

16. A method according to claim 1, wherein the difference of isoelectric points between the protein and the Met-protein is at least 0.1.

17. A method according to claim 1, wherein the difference of isoelectric points between the protein and the Met-protein is between 0.01 and 0.2.

18. A method according to claim 1, wherein the protein and the Met-protein are non-glycosylated.

19. A method according to claim 1, wherein the protein is a cytokine.

20. A method according to claim 19, wherein cytokine is an interleukin-2.

21. A method according to claim 20, wherein the interleukin-2 is a non-glycosylated protein having the amino acid sequence

```
           1
X—Ala Pro Thr Ser Ser Ser Thr Lys Lys Thr Gln Leu Gln

20
Leu Glu His Leu Leu Asp Leu Gln Met Ile Leu Asn

Gly Ile Asn Asn Tyr Lys Asn Pro Lys Leu Thr Arg Met

40
Leu Thr Phe Lys Phe Tyr Met Pro Lys Lys Ala Thr Glu

Leu Lys His Leu Gln Cys Leu Glu Glu Glu Leu Lys Pro

Leu Glu Glu Val Leu Asn Leu Ala Gln Ser Lys Asn Phe

80
His Leu Arg Pro Arg Asp Leu Ile Ser Asn Ile Asn Val

100
Ile Val Leu Glu Leu Lys Gly Ser Glu Thr Thr Phe Met

Cys Glu Tyr Ala Asp Glu Thr Ala Thr Ile Val Glu Phe

120
Leu Asn Arg Trp Ile Thr Phe Cys Gln Ser Ile Ile Ser

133
Thr Leu Thr
``` where X represents a hydrogen atom.

22. A method according to claim 19, wherein the cytokine is an interferon.

23. A method according to claim 22, wherein the interferon is an interferon-α.

24. A method according to claim 23, wherein the interferon—is a non-glycosylated interferon—A consisting of the amino acid sequence

```
           1
X—Cys Asp Leu Pro Gln Thr His Ser Leu Gly Ser Arg Arg

210
Thr Leu Met Leu Leu Ala Gln Met Arg Lys Ile Ser Leu

Phe Ser Cys Leu Lys Asp Arg His Asp Phe Gly Phe Pro

40
Gln Glu Glu Phe Gly Asn Gln Phe Gln Lys Ala Glu Thr

60
Ile Pro Val Leu His Glu Met Ile Gln Gln Ile Phe Asn

Leu Phe Ser Thr Lys Asp Ser Ser Ala Ala Trp Asp Glu

80
Thr Leu Leu Asp Lys Phe Tyr Thr Glu Leu Tyr Gln Gln

100
Leu Asn Asp Leu Glu Ala Cys Val Ile Gln Gly Val Gly

Val Thr Glu Thr Pro Leu Met Lys Glu Asp Ser Ile Leu
           120

Ala Val Arg Lys Tyr Phe Gln Arg Ile Thr Leu Tyr Leu

140
Lys Glu Lys Lys Tyr Ser Pro Cys Ala Trp Glu Val Val

Arg Ala Glu Ile Met Arg Ser Phe Ser Leu Ser Thr Asn 160           165
Leu Gln Glu Ser Leu Arg Ser Lys Glu
``` wherein X represents a hydrogen atom.

25. A method according to claim 1, wherein the mixture is a mixture of the protein and the Met-protein having a purity of not less than 50%.

26. A method according to claim 1, wherein the mixture is a mixture of the protein and the Met-protein having a purity of not less than 99%.

27. A method according to claim 1, wherein a non-glycosylated interleukin-2 and a Met-protein having the amino acid sequence of the interleukin-2 and bearing an additional methionine residue at the amino terminus are separated from each other by subjecting a mixture comprising the interleukin-2 and the Met-protein to a charged carrier selected from the group consisting of chromato focusing, fast protein liquid chromatography, diethylaminoethyl-ion exchange chromatography and sulphoropyl-ion exchange chromatography.

28. A method according to claim 27, wherein the non-glycosylated interleukin-2 consists of the amino acid sequence:

```
        1
X—Ala Pro Thr Ser Ser Ser Thr Lys Lys Thr Gln Leu Gln
                        20
Leu Glu His Leu Leu Leu Asp Leu Gln Met Ile Leu Asn

Gly Ile Asn Asn Tyr Lys Asn Pro Lys Leu Thr Arg Met
40
Leu Thr Phe Lys Phe Tyr Met Pro Lys Lys Ala Thr Glu
                        60
Leu Lys His Leu Gln Cys Leu Glu Glu Glu Leu Lys Pro

Leu Glu Glu Val Leu Asn Leu Ala Gln Ser Lys Asn Phe
    80
His Leu Arg Pro Arg Asp Leu Ile Ser Asn Ile Asn Val
                    100
Ile Val Leu Glu Leu Lys Gly Ser Glu Thr Thr Phe Met

Cys Glu Tyr Ala Asp Glu Thr Ala Thr Ile Val Glu Phe
    120
Leu Asn Arg Trp Ile Thr Phe Cys Gln Ser Ile Ile Ser
    133
Thr Leu Thr
``` where X means a hydrogen atom.

29. A method according to claim 1, wherein a non-glycosylated interferon-αA and a protein bearing an additional methionine residue at the amino terminus of said interferon-αA are separated from each other by subjecting a mixture comprising the interferon-αA and the protein to fast protein liquid chromatography.

30. A method according to claim 29, wherein the non-glycosylated interferon-αA consists of the amino acid sequence:

```
    1
X—Cys Asp Leu Pro Gln Thr His Ser Leu Gly Ser Arg Arg
                    20
Thr Leu Met Leu Leu Ala Gln Met Arg Lys Ile Ser Leu

Phe Ser Cys Leu Lys Asp Arg His Asp Phe Gly Phe Pro
        40
Gln Glu Glu Phe Gly Asn Gln Phe Gln Lys Ala Glu Thr
                60
Ile Pro Val Leu His Glu Met Ile Gln Gln Ile Phe Asn

Leu Phe Ser Thr Lys Asp Ser Ser Ala Ala Trp Asp Glu
    80
Thr Leu Leu Asp Lys Phe Tyr Thr Glu Leu Tyr Gln Gln
                    100
Leu Asn Asp Leu Glu Ala Cys Val Ile Gln Gly Val Gly

Val Thr Glu Thr Pro Leu Met Lys Glu Asp Ser Ile Leu
        120
Ala Val Arg Lys Tyr Phe Gln Arg Ile Thr Leu Tyr Leu
                    140
Lys Glu Lys Lys Tyr Ser Pro Cys Ala Trp Glu Val Val

Arg Ala Glu Ile Met Arg Ser Phe Ser Leu Ser Thr Asn
        160         165
Leu Gln Glu Ser Leu Arg Ser Lys Glu,
``` where X means a hydrogen atom.

31. A process for isolating hTNF from a mixture of hTNF and N-terminal methionine-containing hTNF comprising subjecting said mixture to cation exchange chromatography over a cation exchanger selected from the group consisting of sulfoaryl and sulfoalkyl groups.

32. The process of claim 31, wherein the purity of the isolated hTNF is about 99%.

* * * * *